United States Patent [19]
Keller

[11] Patent Number: 5,370,642
[45] Date of Patent: Dec. 6, 1994

[54] METHOD OF LASER COSMETIC SURGERY

[76] Inventor: Gregory S. Keller, 2323 De La Vina, #105, Santa Barbara, Calif. 93105

[21] Appl. No.: 102,851

[22] Filed: Aug. 2, 1993

Related U.S. Application Data

[63] Continuation of Ser. No. 766,638, Sep. 25, 1991, abandoned.

[51] Int. Cl.$^5$ .............................................. A61B 17/36
[52] U.S. Cl. ......................................... 606/9; 128/898
[58] Field of Search ..................... 606/9, 10, 15, 16; 128/898

[56] References Cited

U.S. PATENT DOCUMENTS

| | | | |
|---|---|---|---|
| 4,519,390 | 5/1985 | Horne | 606/15 |
| 4,627,435 | 12/1986 | Hoskin | 606/16 X |
| 4,791,927 | 12/1988 | Menger | 606/10 X |

FOREIGN PATENT DOCUMENTS

| | | | |
|---|---|---|---|
| 1512572 | 10/1989 | U.S.S.R. | 128/898 |
| 1595481 | 9/1990 | U.S.S.R. | 606/9 |
| 1621901 | 1/1991 | U.S.S.R. | 128/898 |

OTHER PUBLICATIONS

Nishisaka et al, Rounded Tip Fiber-Optics, *The Journal of Japan Society and Laser Medicine*, 1984, p. 178.

*Primary Examiner*—Randall L. Green
*Assistant Examiner*—Mary Beth Jones
*Attorney, Agent, or Firm*—Lyon & Lyon

[57] ABSTRACT

Laser surgery is utilized to perform cosmetic surgery. A quartz fiber is used to direct the laser energy to the target area for the incision, division or resection of tissue. An endoscope may be utilized in conjunction with the quartz fiber to perform the cosmetic surgical techniques. One application utilizes laser energy to eliminate glabellar frown lines and/or forehead wrinkles. Another application employs laser energy to rectify brow descent. A further application uses laser energy to perform a neck lift. In yet another application, laser energy is utilized to reduce nasolabial folds. The use of laser energy in cosmetic surgical procedures greatly reduces the size of the incision required in the skin to perform cosmetic surgical procedures, and as a result greatly reduces the risks of potential complications.

6 Claims, 2 Drawing Sheets

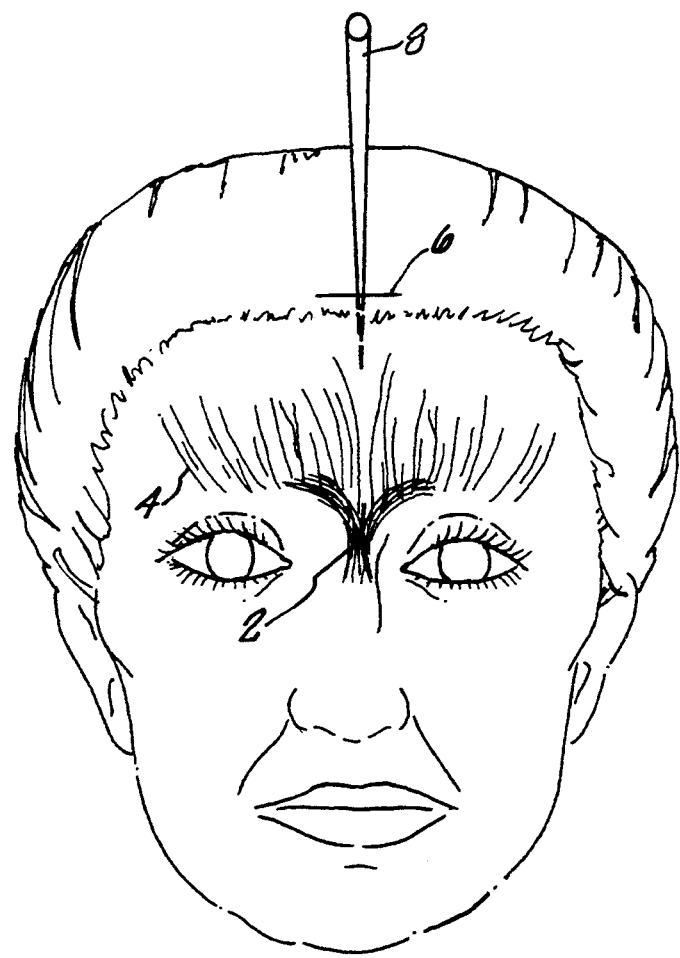
FIG_1
FIG_2

METHOD OF LASER COSMETIC SURGERY

This is a continuation of copending application(s) Ser. No. 07/766,638 filed on Sep. 25, 1991, now abandoned.

BACKGROUND OF THE INVENTION

The field of the present invention is cosmetic surgery.

In recent years, laser technology has been utilized in a variety of applications in industry, surveying, communications and the medical field. In the field of cosmetic surgery, however, standard procedures typically involve extensive use of scalpels for incising, dividing and resecting tissue. Depending upon the particular procedure, disadvantageous complications may result including scarring, nerve damage and reduced blood flow to the affected area which can result in skin slough.

For example, to remove glabellar frown lines (between the eyebrows) and forehead wrinkles, standard cosmetic surgical technique involves an extensive procedure called a forehead lift which entails a large incision that extends from ear to ear over the top of the forehead. The forehead lift is particularly disadvantageous because it opens the patient up widely requiring the physician to stop bleeders and risk cauterizing nerves. Since this procedure creates a large thin skin flap and reduces the blood supply to the skin, there is also an increased risk of skin slough and alopecia (balding). An alternate procedure for removing glabellar frown lines and forehead wrinkles is collagen treatment. However, this treatment is temporary at best and also involves a risk of allergic reaction. Moreover, collagen has been reported to cause autoimmune disease and blindness.

SUMMARY OF THE INVENTION

The present invention is directed to a method of cosmetic surgery utilizing laser energy to incise, divide or resect tissue as necessary to perform a particular cosmetic surgical procedure. The use of laser energy instead of a scalpel greatly reduces the size of the incision necessary to perform cosmetic surgical procedures and also significantly diminishes the risk of complications. An endoscope with a channel for delivering the laser transmitting means can further reduce the size of the incision necessary to perform cosmetic surgical procedures.

BRIEF DESCRIPTION OF THE DRAWINGS

FIG. 1 is a frontal view of a human head with a small incision in the forehead to insert an endolaser for removal of glabellar frown lines and forehead wrinkles.

FIG. 2 is a lateral view of a human head with a small incision in the temple to insert an endolaser for removal of crows feet.

DESCRIPTION OF THE PREFERRED EMBODIMENTS

Figure 3:
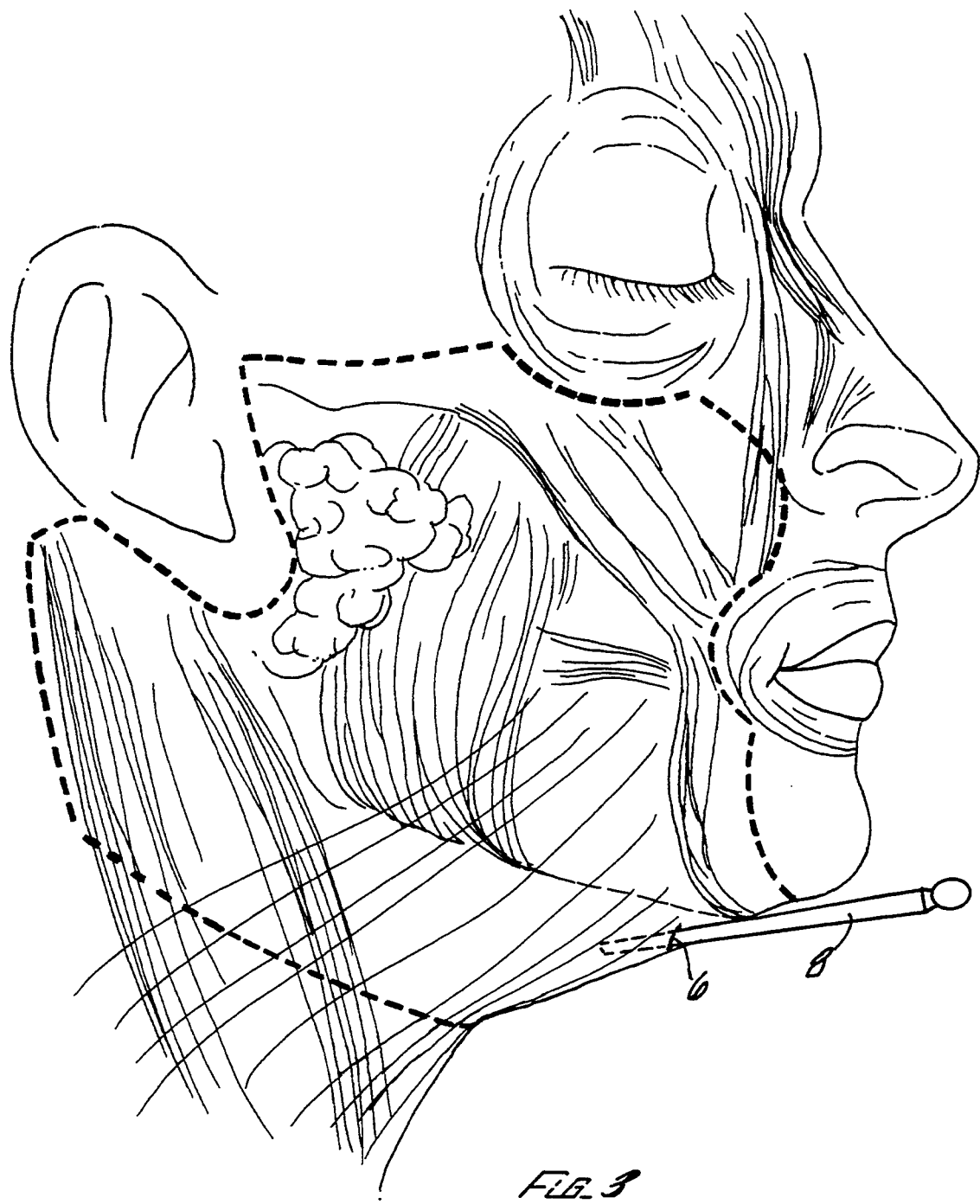
FIG. 3 is a lateral view of a human head with a small incision in the neck to insert an endolaser for performing a neck lift.

While the invention has application with utility and advantage in a plethora of cosmetic surgical procedures, the following will describe the invention in four such applications. All four applications utilize a laser energy source which is principally transmitted to a target area usually by, but not limited to, a quartz fiber with a 300 to 700 micron diameter and a 100 to 250 micron tip. The laser energy wavelength used is typically, but not limited to, 532 to 1060 nm. In a specially preferred embodiment, a 400 micron diameter quartz fiber with a 100 micron tip is utilized with a laser having a 532 nm. Wavelength appears to produce the best results. An optional means for directing the laser transmitting means to the target area is an endolaser which is composed of an endoscope with or without a channel containing the laser transmitting means and/or balloon retractors that allow retraction in two directions.

FIG. 1 illustrates a frontal view of a human head with glabellar frown lines 2 and forehead wrinkles 4. The supraorbital and supratrochlear foramen and nerve courses are marked. A small incision 6 or pair of incisions are made at or behind the hair line for the insertion of the endolaser 8. If the quartz fiber is used without an endoscope, a larger incision is required. Using hooks, retractors, a bivalve speculum, and the endolaser or quartz fiber, a supragaleal elevation of the forehead is undertaken.

The fusion layer of fascia is found and separated either above the periosteum with the laser or below the periosteal layer with an elevator. Using retraction and/or a balloon around the endoscope, the corrugator and procerus muscles are divided and/or resected with the laser, preserving, when possible, the supratrochlear nerves. Following this the frontalis muscle is divided in similar fashion. Retraction may be with a wire frame retractor. The supraorbital nerve corridor is preserved. Fascia is used to fill any defects. If the mid-brow/glabellar area is depressed a calibrated resection of forehead and/or frontal hair bearing skin is resected and galea and skin closed. If necessary, the wound may be drained. The incision is then closed utilizing a galeal as well as a cutaneous closure.

In males with alopecia, a similar procedure is performed, but the approach is through a unilateral or bilateral temporal incision.

FIG. 2 depicts a lateral view of a human head with brow descent, skin over the lateral eye and crow's feet 10. To diminish these problems, the temple and lateral brow may be elevated. The incision lines and the supraorbital nerve course and a vertical line extending from the lateral canthus are marked. A small incision 6 or pair of incisions are made in the hair of the temple for the insertion of the endolaser 8. Again, when using only a quartz fiber a larger incision is required.

The deep temporal fascial layer is developed using the hooks and/or retractors and/or balloon retractors. Once the avascular plane is found, the dissection under the danger area of the frontal branch of the facial nerve is performed with blunt dissection with small dissecting sponges. The fusion layer with the galea is divided and, over the frontal and/or zygomatic bone the supragaleal plane developed with the laser or a subgaleal plane developed with the elevator. The corridor of the supraorbital nerve is avoided. The fusion layer of fascia below the brow is divided either in a supraperiosteal plane with the laser or blunt instrument or in the subperiosteal plane with the elevator.

The frontalis muscle is incised three centimeters above the brow and medial to the vertical line from the lateral canthus. A suture is placed from an area immediately below the brow to the temporalis fascia to achieve a predetermined elevation. Resection of skin and/or hair is rarely necessary, but performed if needed. The incision is closed at the galeal and skin levels.

FIG. 3 shows a lateral view of a human head with a small incision in the neck 6 for insertion of an endolaser 8 for performing the inventive method of the platysma muscle and necklift.

Markings are made for the submental incision, the course of the facial nerve, the submental foramen, the platysmal bands, and the platysmal incision. A submental incision is performed and liposuction carried out in the usual manner. Dissection is carried downward with the laser to divide the tunnels. A strip of platysma and subplatysmal fat is then removed in vertical fashion with the laser. The endoscope is then placed horizontally in the tunnels overlying the platysma and with retraction from a balloon retractor and/or retractors, the platysma is divided and/or bluntly undermined. A corset platysmaplasty is then formed in the midline and the submental incision closed.

The fourth example of an endolaser approach to cosmetic surgery involves reduction of nasolabial folds. An eye protection device is placed. Incision lines and the infraorbital foramen and nerve corridor are marked. A transconjunctival or eyelid skin incision is performed utilizing the laser or knive. Dissection is usually carried preseptally and orbital septum divided and access obtained to the cheek. Using either blunt or laser dissection the nasolabial fold area is identified using the endoscope, retractors, balloon retractors, instruments, and laser. The soft tissue of the nasolabial fold areas is then sutured upward. The incisions are closed.

In contrast to previous procedures, the combination of laser and endoscope allows this procedure to be performed under direct vision through smaller incisions inside the eye, a cosmetically superior situation.

While various apparatus and methods of treatment have been described in order to make the invention known to those skilled in the art, it should be readily apparent that many more modifications of the techniques disclosed are possible without departing from the inventive concepts contained herein. The foregoing description, therefore, should be taken as illustrative and not limiting in any sense.

I claim:

1. A method of cosmetic surgery for the treatment of frown lines and forehead wrinkles comprising:
   marking on the skin the supraorbital and supratrochlear formen and nerve courses;
   performing at least one small incision in the skin near the hair line for inserting a laser transmitting means beneath the skin;
   inserting a laser transmitting means beneath the skin; a
   directing the laser energy from the laser transmitting means to;
   separate the fusion layer of fascia either above the periosteum,
   divide and/or resect the corrugator and procerus muscles, and wherein the method further includes
   divide the frontalis muscle with the laser-transmitting means; and
   closing the incision.

2. The method of claim 1 wherein the laser-transmitting means comprises a quartz fiber.

3. The method of claim 2 wherein the quartz fiber has a diameter between 300 and 700 microns and a 100 to 250 micron tip.

4. The method of claim 2 wherein the quartz fiber has a 400 micron diameter and a 100 micron tip.

5. The method of claim 1 wherein the laser energy is characterized by a wavelength between 532 to 1060 nm.

6. The method of claim 1 wherein the laser transmitting means is an endolaser comprising an endoscope with a channel containing a laser transmitting quartz fiber.

* * * * *